(12) United States Patent
Pines

(10) Patent No.: US 10,517,703 B2
(45) Date of Patent: Dec. 31, 2019

(54) DENTAL FLOSSING DEVICE

(71) Applicant: FLEXI FLOSS LTD., Haifa (IL)

(72) Inventor: Erella Pines, Pardes Hanna (IL)

(73) Assignee: FLEXI FLOSS LTD., Haifa (IL)

( * ) Notice: Subject to any disclaimer, the term of this patent is extended or adjusted under 35 U.S.C. 154(b) by 536 days.

(21) Appl. No.: 15/232,110

(22) Filed: Aug. 9, 2016

(65) Prior Publication Data

US 2016/0346067 A1 Dec. 1, 2016

Related U.S. Application Data

(63) Continuation-in-part of application No. 14/661,640, filed on Mar. 18, 2015, now abandoned.
(60) Provisional application No. 61/954,736, filed on Mar. 18, 2014.

(51) Int. Cl.
| | | |
|---|---|---|
| A61C 15/00 | (2006.01) | |
| A61C 15/04 | (2006.01) | |
| A61C 19/06 | (2006.01) | |

(52) U.S. Cl.
CPC .......... *A61C 15/046* (2013.01); *A61C 19/063* (2013.01)

(58) Field of Classification Search
CPC ..... A61C 15/046; A61C 15/041; A61C 15/00; A61C 15/04; A61C 15/042; A61C 19/063
See application file for complete search history.

(56) References Cited

U.S. PATENT DOCUMENTS

| | | |
|---|---|---|
| 1,989,895 A | 2/1935 | Van Gilder |
| 2,180,522 A | 11/1939 | Henne |
| 3,247,857 A | 4/1966 | Kanbar |

(Continued)

FOREIGN PATENT DOCUMENTS

| | | |
|---|---|---|
| GB | 2349338 A | 11/2000 |
| KR | 20110132255 A | 12/2011 |
| WO | 2011152637 A2 | 12/2011 |

OTHER PUBLICATIONS

English Language Abstract, KR 2011 0132255 A.

(Continued)

*Primary Examiner* — Rachel R Steitz

(74) *Attorney, Agent, or Firm* — Browdy and Neimark, PLLC

(57) ABSTRACT

A dental flossing device is made of an elastic material. Its central structure is a resiliently stretchable elastic, bridge strip with a cross section having different shapes. When stretched, the strip has a changeable diameter to help remove debris between teeth. The strip includes corrugations or spirals along its length and may include different drugs or flavors to give the user a medicine or a taste while cleaning the teeth. At each end of the strip, there is an elastic opposing handle. Handles may be bridged by two or more stretchable strips. The two handles may have different dimensions and thicknesses, as well as different profiles; they may be resiliently stretchable so as to serve themselves as additional flossing members. The device may comprise more than two handles and more than one flossing strip and thus may form various configurations such as ring-like, chain-like, star-like, etc. A method for making the dental flossing device out of the elastic material includes molding the elastic, bridge strip and integrally molding the elastic opposing handles at opposite ends of the strip.

16 Claims, 9 Drawing Sheets

(56) References Cited

U.S. PATENT DOCUMENTS

| | | | |
|---|---|---|---|
| 3,511,249 A | 5/1970 | Baitz | |
| 3,802,445 A | 4/1974 | Wesley | |
| 4,016,892 A | 4/1977 | Chodorow | |
| 4,034,770 A | 7/1977 | Trecker | |
| 4,191,291 A | 3/1980 | Brown | |
| 4,262,799 A | 4/1981 | Perrett | |
| 4,523,600 A | 6/1985 | Donovan | |
| 4,638,824 A | 1/1987 | De La Hoz | |
| 4,836,226 A | 6/1989 | Wolak | |
| 5,038,805 A | 8/1991 | Lee | |
| 5,086,792 A | 2/1992 | Chodorow | |
| 5,435,330 A | 7/1995 | Dix | |
| 5,454,386 A | 10/1995 | Dix | |
| 5,799,673 A | 9/1998 | Amendola et al. | |
| 5,871,021 A | 2/1999 | Fong | |
| D406,395 S | 3/1999 | Marin | |
| 5,893,379 A | 4/1999 | Ghamaty-Azimi | |
| 5,947,132 A | 9/1999 | Swanson | |
| 5,971,149 A | 10/1999 | Sakurai | |
| 6,003,525 A * | 12/1999 | Katz | A61C 15/041 132/321 |
| 6,152,147 A | 11/2000 | Sanchez | |
| 6,161,555 A | 12/2000 | Chen | |
| 6,371,133 B1 * | 4/2002 | Gant | A61C 15/041 132/321 |
| 6,397,853 B1 | 6/2002 | Lovick | |
| 6,604,534 B2 | 8/2003 | Hill | |
| 6,672,316 B1 | 1/2004 | Weihrauch | |
| 6,685,023 B2 | 2/2004 | Bleggi et al. | |
| 7,146,987 B2 | 12/2006 | Tse | |
| 7,281,541 B2 | 10/2007 | Lorch | |
| 7,631,650 B2 * | 12/2009 | Major | A61C 15/046 132/323 |
| 8,042,556 B2 | 10/2011 | Bowsher | |
| 2004/0250834 A1 | 12/2004 | Bowsher | |
| 2006/0201530 A1 | 9/2006 | Monroe | |
| 2007/0138042 A1 | 6/2007 | Wood | |
| 2008/0113315 A1 | 5/2008 | Beggs | |
| 2008/0163888 A1 | 7/2008 | Chen | |
| 2008/0314406 A1 | 12/2008 | Barrie | |
| 2009/0198262 A1 | 8/2009 | Rosenblood et al. | |
| 2012/0080050 A1 * | 4/2012 | Kazes | A61C 15/02 132/329 |
| 2013/0061864 A1 | 3/2013 | Oermae Teppo | |

OTHER PUBLICATIONS

Dentistryiq Editors. Flexible, Medical-grade Silicone Rubber Floss Introduced. Product announcement/press release. Dentistry IQ. Jun. 17, 2014 [retrieved on Nov. 8, 2015]. Retrieved from the internet: <URL: http://www .dentistryiq .com/ articles/20 14/06/silicone-rubberfloss-debuts.html>, entire document.

International Search Report and the Written Opinion of the International Searching Authority in PCT/US2015/051081 dated Dec. 11, 2015.

* cited by examiner

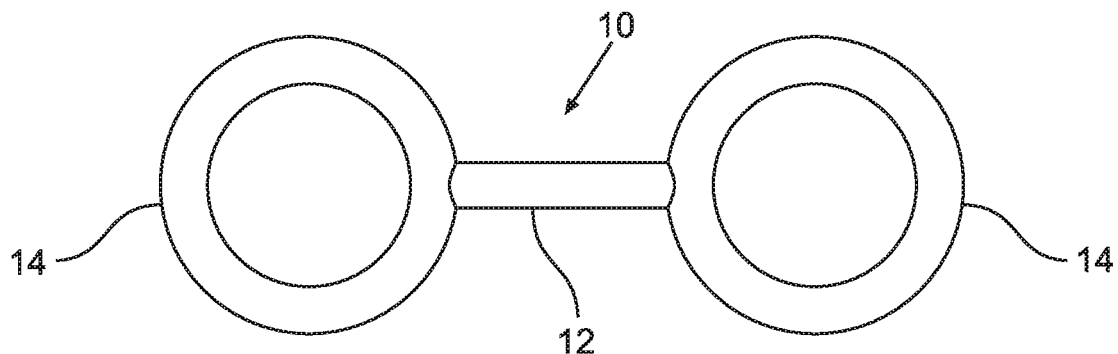
FIG. 1
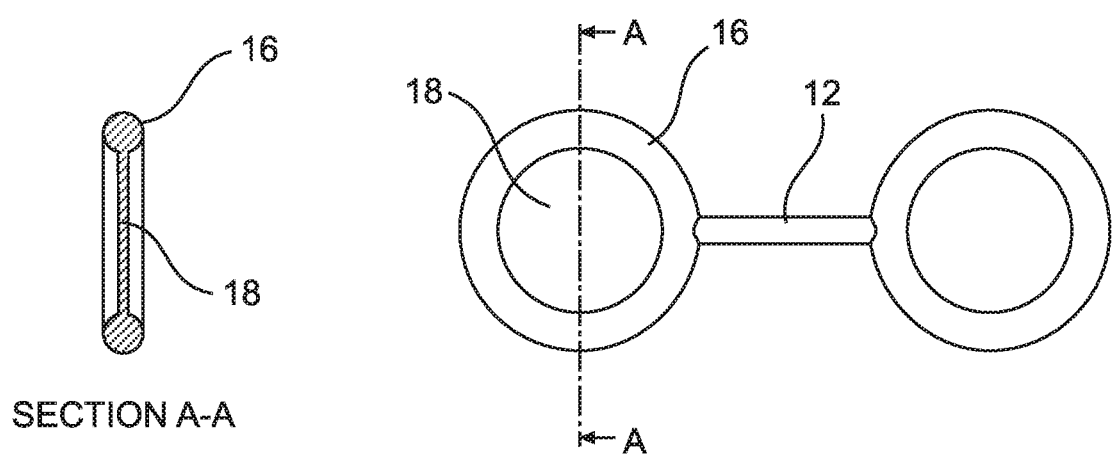
SECTION A-A
FIG. 2B
FIG. 2A
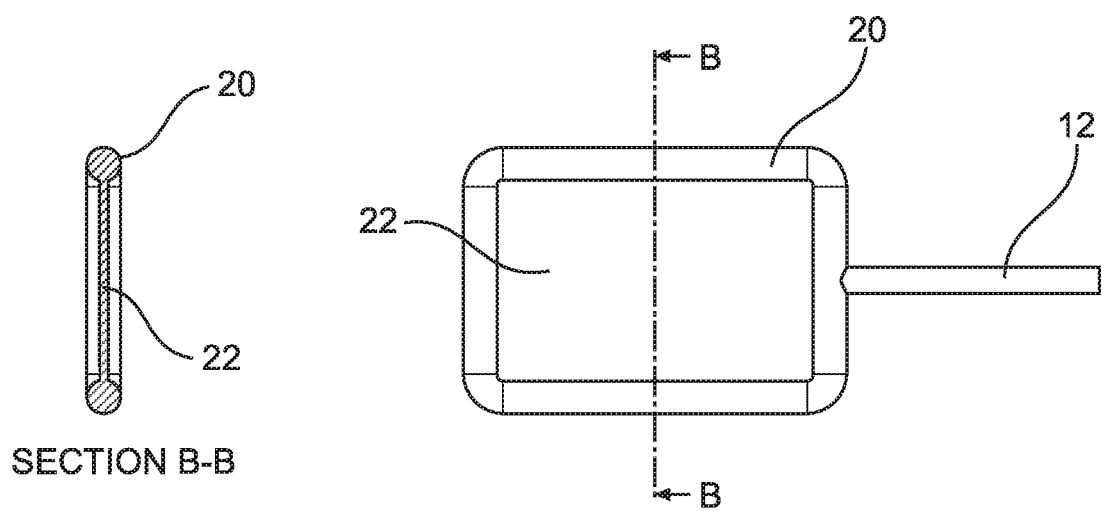
SECTION B-B
FIG. 2D
FIG. 2C

DENTAL FLOSSING DEVICE

CROSS-REFERENCE TO RELATED APPLICATIONS

This application is a Continuation in Part Patent Application of U.S. Ser. No. 14/661,640 which claims priority of U.S. Provisional Application No. 61/954,736 entitled "DENTAL FLOSSING DEVICE," filed Mar. 18, 2014, the contents of which two applications are incorporated herein by reference in their entirety.

BACKGROUND OF THE INVENTION

Field of the Invention

The present invention relates to dental hygiene devices. Specifically, the field of the invention relates to a dental floss device that is held by a user to clean spaces between the user's teeth. Proper use assures removal of debris from between the user's teeth.

Discussion of Background Information

Dental flossing is recommended by dental professionals as a necessary daily treatment for maintaining optimal dental hygiene. If done properly, flossing can prevent the onset of gum diseases, such as gingivitis, and cavities in flossed areas.

A dental floss is typically structured from a soft thread of fibers which is inserted into inter-proximal spaces (IPSs) of the user's teeth to allow scraping of the fiber across the surface of the tooth. The scraping motion loosens debris from the dental surface, usually removing the debris from the flossed section and leaving the surface in a cleaner state, thus resulting in better oral hygiene.

However, acceptance of flossing by the general public has been limited, even after decades of warnings and educational campaigns from dental associations. People find proper flossing tedious, uncomfortable, and difficult. Many people have sensitivity and bleeding gums. Thus, flossing is not a generally accepted method of oral hygiene. For example, the younger population and people with sensitive gingiva are not using this modality. To reach and adequately floss all necessary places with current flossing devices and materials requires time, manual dexterity, and discipline, with typical discomfort, pain and occasional bleeding. Theses results cause too many people to refrain from using this important modality.

Many attempts have been made in this field to make flossing more acceptable by providing different structures and electromechanical devices. Nevertheless, flossing is not utilized by the majority of the people as a daily routine.

One known flossing device is disclosed in South Korean Published Patent Application No. KR2011-0132255 dated Dec. 7, 2011. While this disclosure addresses some of the drawbacks of the prior art, it does not address them in the same manner as the present invention which is described in greater detail below.

Another known flossing device is disclosed in US 2012/0080050 to Kazes dated Dec. 13, 2011. The Kazes device constitutes a generally rigid flossing stick having some flexibility to introduce it between the teeth. However, the Kazes device does not address all the mentioned drawbacks of the prior art since it physically remains a flossing stick which is usually inserted into IPS from the side. The Kazes flossing device, though being flexible, remains rigid and has its natural limitations and drawbacks—e.g. difficulty to insert it between closely adjoining teeth, pressing action of such a rigid device onto the food residuals, danger of damaging the gums, etc.

Therefore, it remains a problem in the dental arts to find a solution that will make flossing a more comfortable and pleasant experience, thus making flossing a more accepted solution to be used by most of the population.

SUMMARY OF THE INVENTION

The present invention is a solution that will make flossing a more comfortable and pleasant experience. As a result of the use of the present invention, it is expected that flossing will become a more accepted dental cleaning solution which will be used by most of the population.

The tooth cleaning apparatus of the present invention includes a plurality of lengths and shapes for opposing, side handles to be gripped by the user's fingers while flossing the teeth. The structure of the present invention includes at least two elastic handles bridged by at least one resiliently stretchable elastic flossing strip.

The elasticity (resilience) of the proposed flossing strip should be understood as a) readiness to large elastic deformations, i.e. ability of the flossing strip to be stretched (elongated) in the range of about 50% to 800% of its initial (original) length under a stress/stretching force applied by fingers of a user, while b) ensuring complete return of the flossing strip to its original length when said stretching force is no longer applied, and ensuring repetitive stretching when the force is applied again. It should be understood that elongation of the flossing strip causes suitable decrease of its cross-section, which fact facilitates introduction of the flossing strip into any IPS and improves cleaning of the IPS.

Different sizes of the proposed device will fit youngsters or adult users, depending upon the size of each person's mouth.

A so-called "basic" proposed dental flossing device (i.e., a basic cell thereof) comprises the two elastic handles bridged by one or more resiliently stretchable elastic flossing strips. Further, the dental flossing device may be "modular", i.e. may comprise more than two said handles and more than one said stretchable flossing strips.

An important feature of the invention is that the flossing strip is resiliently stretchable due to being elastic. It is made from a strong elastic material which cannot be torn while being stretched and inserted into the inter-proximal spaces (IPSs) of the teeth. Also, the elastic material used for manufacturing the device, is bio-compatible.

The flossing strip, whenever mentioned in the present description as is, or with the adjectives "stretchable", "resiliently stretchable", "elastic" and/or "resilient", should always be understood as an easily and repeatedly stretchable by user's fingers, elastic and resilient flossing strip made of a suitable material.

In one embodiment of the invention, the whole dental flossing device may be a resiliently stretchable elastic device integrally manufactured from the same material as its stretchable elastic flossing strip(s). It is proposed that the handles (whenever made from the same material) are configured to serve as additional resiliently stretchable flossing members, when desired or necessary.

The handles may be manufactured in the form of loops having a circular, a rectangular or any other shape.

The material suitable for the stretchable flossing strip/s of the device (as well as for the whole dental flossing device, if manufactured in such an integral embodiment) may for example be a silicone rubber or a so-called medical silicone rubber, a sample of which is elastically and resiliently stretchable up to 700% or even up to 800% of its original size when subjected to a stretching force.

Silicone flossing strips will have a higher coefficient of friction than conventional flosses made, for example, of teflon or nylon. Moreover, silicone flossing strips will accumulate some static electrical charge, which will be advantageous for catching and removing "debris" from IPS.

Alternatively, the stretchable, elastic (resilient) material may be a natural rubber (latex), SBR, (Styrene Butadiene Rubber), Nitril rubber, EPDM (Ethylene Propylene Diene Monomer rubber), or any other organic rubber. Still further, the material may be selected from a list of Thermo Plastic Elastomers (TPE) like SOFPRENE (SBS) and LAPRENE (SEBS), Xantropene or the like.

Recommended properties of the material are high stretchability and high elasticity (resilience). The recommended stretchability (elongation ability, ability to elastic deformations) can be defined from about 50% up to about 800%.

Large elastic deformations of a rod can be described by the following formula:

$$\Delta d = -d(1-(1+\Delta L/L)^{-v}) \quad (1)$$

Where:
d—original diameter of the rod
$\Delta d$—rod diameter change
v—Poisson's ratio
L—original length, before stretch
$\Delta L$—the change of length The value of $\Delta d$ is negative since it decreases with increase of length.

According to formula (1), the following changes in the diameter of a cylindrical elastic member may be predicted and then achieved for two exemplary dimensions of the proposed stretchable dental flossing member. In this specific example, the dental flossing member is a resiliently stretchable, elastic flossing strip having initial length L and forming part of a dental flossing device made of silicone rubber:

For the initial diameter 1.1 mm of the flossing member:
    the 200% stretching gives a new diameter 0.56 mm of the flossing member,
    the 700% stretching gives a new diameter 0.37 mm of the flossing member.
For the initial diameter 2.0 mm of the flossing member:
    the 200% stretching gives a new diameter 1.02 mm of the flossing member,
    the 700% stretching gives a new diameter 0.70 mm of the flossing member.

As can be seen, the substantial changes of the flossing member's diameter, which can be achieved when stretching the new proposed device, allow easily introducing the flossing strip into a specific IPS of interest without purchasing a different flossing device. Moreover, the floss diameter that repeatedly changes its value under a changing force applied to the flossing device (upon being inserted in an IPS), will allow improving the cleaning effect of the flossing member in the IPS.

It should be emphasized, that presence of at least one stretchable elastic member in the flossing device (e.g., at least one such flossing strip) ensures dramatic improvement in the flossing device operation. In other words, such a stretchable flossing strip allows easily introducing it in any IPS, since the stretchable strip will be adjusted to any specific IPS by the user who controls thickness of the strip by stretching it. When introduced (from above, as any dental floss), the stretching force may be reduced up to zero and the flossing strip may return to its original shape owing to its resiliency, than it may be stretched again, then moved back and force by the user, and so on. It has been found and shown by the Inventors, that such repetitive actions of stretching and shrinkage, optionally combined with moving the strip back and forth in IPS, result in effectively catching and removing the debris from the IPS. The same applies to any other stretchable and resilient member of the proposed device (for example, one or more of the handles, if they are also stretchable and resilient).

In one embodiment of the invention, the tooth cleaning apparatus (the dental flossing device) of the present invention includes two handles and at least one flossing strip bridging the two handles, wherein both the handles and the strip are resiliently elastic and stretchable.

In one further embodiment, the structure of the inventive device includes two or more stretchable elastic flossing strips bridging the two handles. For example, the two flossing strips may in parallel bridge the two handles.

In another embodiment, the device may comprise more than two said stretchable flossing strips arranged to interconnect more than two said handles. In one example, more than two said flossing strips and more than two said handles form a ring-like or a matrix-like configuration. In another example, such multiple strips and handles form a star-like configuration. In yet a further example, the multiple strips and handles form a chain-like configuration. Various combined configurations, formed by multiple stretchable strips and handles, are also possible. Such configurations are easy to pack, sell, store and use.

In still a further embodiment of the invention, different members of the dental flossing device may have different thicknesses at their initial state (i.e., before any stretching action is applied to the device). Such different thicknesses of different members allow easily introducing one or another of such members into inter proximal spaces IPS having any dimensions—from very crowded to very loose ones. (The members of the flossing device are at least said flossing strip and said two handles. Other configurations of the device may comprise more members.) The proposed device thus becomes a universal tool which, once bought, may be used by any specific user for flossing between regular, crowded and/or spaced teeth, as required.

In a variety of embodiments, various designs and/or dimensions of the dental flossing device and its specific members will be described and illustrated.

In a specific example, the two loop-shaped handles of the device may have different thicknesses, dimensions/diameters and/or different profiles (so that they themselves can be used as different flossing members or quazi-strips). Moreover, the thickness of any of the handles may differ from thickness of the stretchable flossing strip(s) interconnecting the two handles.

It should be noted that the flossing strip(s) may have various profiles, lengths, thicknesses so as to suit to different inter proximal spaces of different users, as well as to different inter proximal spaces of one and the same user.

In yet a further example, said at least one flossing strip may have thickness that changes along the strip's length. The purpose of such a structure is to provide a user with an option to introduce the stretchable flossing strip between the user's teeth at such a region of the strip, which maximally suits for comfortable and effective insertion and flossing. Once holding such a non-uniform flossing strip, the user may introduce a thinner region of the strip between the teeth, and then move the stretchable strip so as to us its thicker region for effective flossing. It should be added that the stretchability/resilience of different members of the dental flossing device, as well as of different sections of the elastic flossing strip may also differ.

In one specific embodiment, at least one stretchable member of the dental flossing device (e.g., one or more of the flossing strips, one or more of the handles,) may be provided with protrusions/filaments made of the same material and having various sizes and shapes, for more effective removal of debris when flossing between the teeth.

The protrusions/filaments may radially extend from the stretchable member in one or more directions. For example, said at least one stretchable strip may be provided with a first group of protrusions and a second group of protrusions, wherein the protrusions of said first and second groups may radially extend from said strip in one plane or in two non-coinciding planes (for instance in two mutually perpendicular planes). In general, N groups of radially extending protrusions may be formed on the stretchable member, which N groups may respectively lay in N non-coinciding planes.

The proposed resiliently stretchable dental flossing device may be wholly or partially chewable and may be adapted to dispense an artificial flavor and/or a medicine.

Other exemplary embodiments and advantages of the present invention may be ascertained by reviewing the present disclosure and the accompanying drawings.

BRIEF DESCRIPTION OF THE DRAWINGS

The present invention is further described in the detailed description which follows, in reference to the noted plurality of drawings by way of nonlimiting examples of embodiments of the present invention, in which like reference numerals represent similar parts throughout the several views of the drawings, and wherein:

FIG. 1 shows a side view of a first embodiment of the invention;

FIG. 2A shows a left side view of a second embodiment of the invention;

FIG. 2B shows a cross-sectional view along line A-A in FIG. 2A;

FIG. 2C shows a left side view of a third embodiment of the invention;

FIG. 2D shows a cross-sectional view along line B-B in FIG. 2C;

FIG. 5B is a perspective view illustrating the use of device 60, 80, 100, 110, 150, 160 or the like.

DETAILED DESCRIPTION OF EXEMPLARY EMBODIMENTS

Figure 3A:
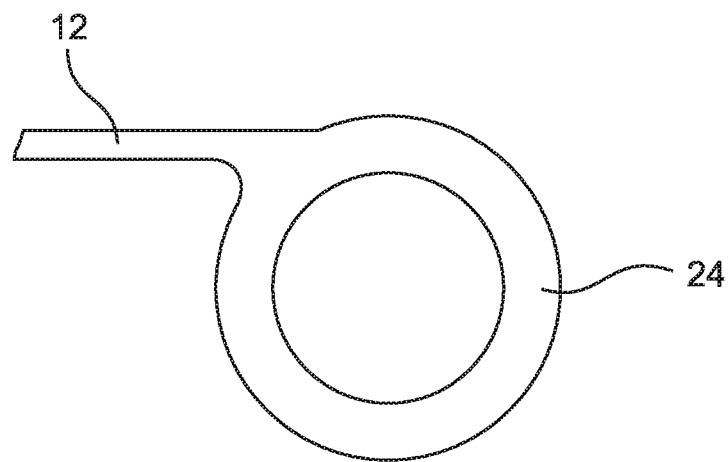
FIG. 3A shows a right side view of a fourth embodiment of the invention.

The particulars shown herein are by way of example and for the purpose of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

A module of the dental flossing device includes a flexible, elastic, bridge strip that can be stretched by a user to be inserted into inter-proximal spaces (IPSs) of the user's teeth. The strip has a right terminal end and a left terminal end. An elastic, right gripping handle is integrally molded with the right terminal end of the strip; and an elastic, left gripping handle is integrally molded with the left terminal end of the strip. The strip and the gripping handles form a single piece out of the same elastic material. For example, the strip has one thickness and each of the gripping handles has a thickness different than the thickness of the strip. The thickness of the gripping handles may be the same or not. Each of the gripping handles may be a hollow ring. Alternatively, each of the gripping handles may be a ring with an elastic web in its center, wherein a thickness of the elastic web is less than the thickness of each of the gripping handles. Further, each of the gripping handles may be a hollow quadrilateral. Alternatively, each of the gripping handles may be a quadrilateral with an elastic web in its center, wherein the thickness of the elastic web is less than the thickness of each of the gripping handles. In one embodiment, the right terminal end of the strip may be molded at a 270-degree point of the right gripping handle while simultaneously the left terminal end of the strip may be molded at a 90-degree point of the left gripping handle.

In another embodiment, the right terminal end of the strip may be molded at a zero-degree point of the right gripping handle. The flexible, elastic, bridge strip may have at least one of, corrugations or spirals, so as to help remove debris between the user's teeth. The corrugations or spirals on the strip may be chewable and dispense either an artificial flavor or a medicine. In a further embodiment, each of the gripping handles may have rays emanating therefrom. The emanating rays may be chewable and dispense either an artificial flavor or a medicine. The dental flossing device may be stored in a carrying case made of plastic, metal, wood or a similar material. The carrying case has two posts configured to retain the gripping handles therein. Multiple modules of the dental flossing device may be molded from the same elastic material and interconnected to form various configurations.

A method of making the dental flossing device includes molding a flexible, elastic, bridge strip that can be stretched by a user to be inserted into inter-proximal spaces (IPSs) of the user's teeth, said strip having a right terminal end and a left terminal end; integrally molding an elastic right gripping handle with the right terminal end of the strip; and integrally molding an elastic left gripping handle with the left terminal end of the strip; wherein the strip and the gripping handles are formed into a single piece out of the same elastic material. The strip may be molded to have one thickness and the two gripping handles—to have a thickness greater than the thickness of the strip. Additional elastic strip(s) and handle(s) may be molded out of the same elastic material and interconnected with the basic elastic strip and handles, thus forming an integral single piece configuration.

In FIG. 1, a first embodiment of a dental flossing device 10 is shown to be made of an elastic material selected from one of: latex, silicone rubber, natural rubber, other synthetic rubbers, thermoplastic polymers, polystyrene, and acetyl polymers such as Delrin® and nylon resins, SBR, Nitril rubber, EPDM, or any other organic rubber, a Thermo Plastic Elastomer (TPE) like SBS, SEBS, Xantropene or the like.

The material suitable for the stretchable flossing strip/s of the device (as well as for the whole dental flossing device), should preferably be elastically and resiliently stretchable up to 700% or even up to 800% of its original size when subjected to a stretching force.

A central structure of the device 10 is a flexible, elastic bridge strip 12, with a cross section having any shape, e.g. round, square, having corrugations, and/or having spirals. The strip 12 can be one strip or two strips or a network of multiple strips. When stretched, the strip 12 has a changeable diameter to help remove debris between a user's teeth. At each terminal end of the strip 12, there is an elastic opposing gripping handle 14 in a shape like a hollow (or solid) ring to fit around a user's finger. The strip 12 has one thickness while each of the opposing handles 14 has a thickness greater than the thickness of the strip 12. The thickness of each of the opposing handles 14 is the same. The strip 12 and the opposing handles 14 are integrally molded in a single piece out of the same elastic material.

A right terminal end of the strip 12 is formed at the 270-degree point of the right handle 14. A left terminal end of the strip 12 is formed at the 90-degree point of the left handle 14. The elastic material allows the user to stretch the strip 12 so that it fits into any space between the user's teeth. More stretching will allow the strip 12 to become thinner, thus fitting into narrower spaces between the teeth.

In FIG. 2A, a left side of a second embodiment is shown in which the strip 12 has a ring-like handle 16 with a thin elastic web 18 in its center. In this second embodiment, each web 18 is gripped by the user between his index finger and his thumb.

FIG. 2B is a cross section taken along line A-A of FIG. 2A and shows the thinness of the web 18 relative to the ring-like handle 16.

In FIG. 2C, a left side of a third embodiment is shown in which the strip 12 has a quadrilateral-shaped handle 20 with a thin elastic web 22 in its center. In this third embodiment, each web 22 is gripped by the user between his index finger and his thumb.

FIG. 2D is a cross section taken along line B-B of FIG. 2C and shows the thinness of the web 22 relative to the quadrilateral-shaped handle 20.

In FIG. 3A, a fourth embodiment is shown in which the strip 12 is formed at the zero-degree point of a right, hollow, ring-like handle 24 which fits around the user's index finger.

Figure 3B:
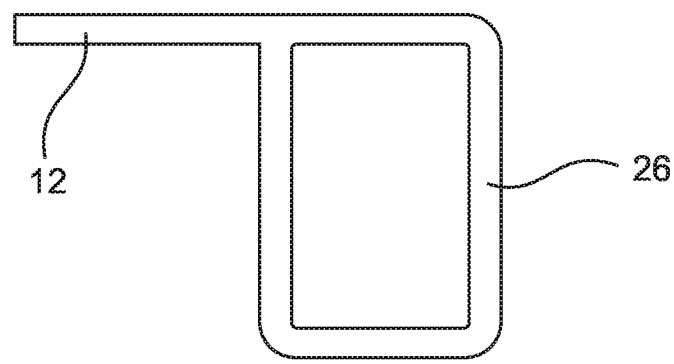
FIG. 3B shows a right side view of a fifth embodiment of the invention.

In FIG. 3B, a fifth embodiment is shown in which the strip 12 is formed at an upper left corner of a right, hollow, quadrilateral-shaped handle 26 which fits around the user's index finger.

Figure 4:
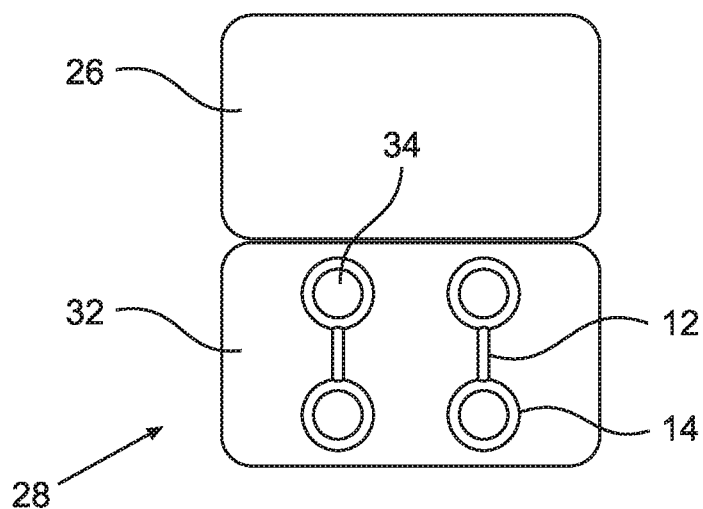
FIG. 4 shows a top plan view of a carrying case for the first embodiment of FIG. 1.

In FIG. 4, a carrying case 28 is made of any suitable material such as metal, plastic, wood, etc., in a size to fit easily into a man's pocket or a woman's hand bag. The case 28 has a top lid 30 and a bottom tray 32 with two posts 34 for receiving the handles 14 of the first embodiment of the dental flossing device 10. The elastic strip 12 extends between the two elastic handles 14. Although two sets of the posts 34 are shown for retaining two devices 10, the case 28 may be configured to handle only one device 10 or three or more devices 10.

Figure 5A:
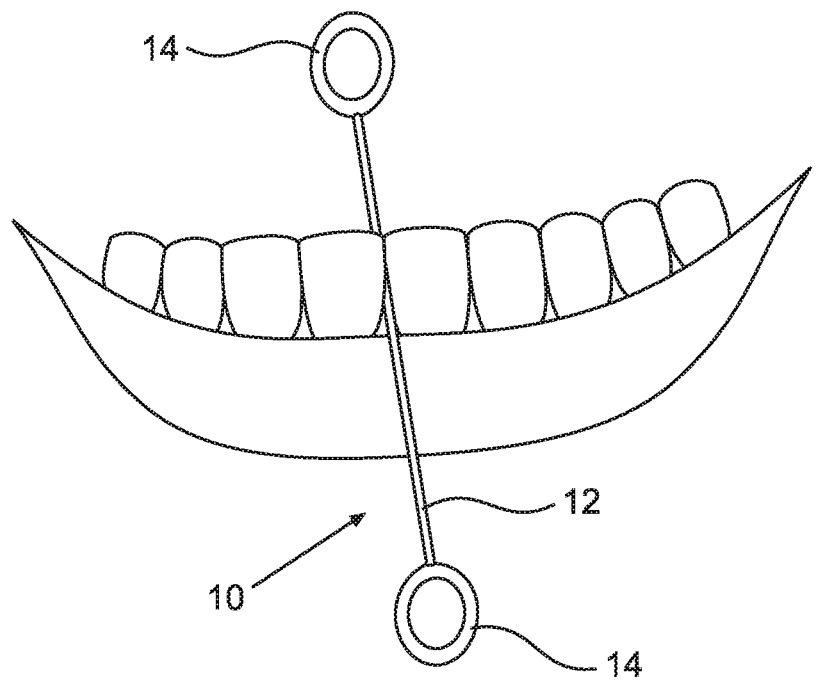
FIG. 5A shows a schematic view of teeth while using device 10 of FIG. 1.

FIG. 5A shows use of the first embodiment of the dental flossing device 10 by the user who has placed, for example, one index finger into one of the ring-like handles 14 and who has also placed the other index finger into the other ring-like handle 14. By pulling his fingers in the opposing elastic handles 14 apart, the user stretches the central elastic strip 12 so that he/she is able to reach into narrow crevices between his teeth in order to remove debris therefrom.

Figure 5B:
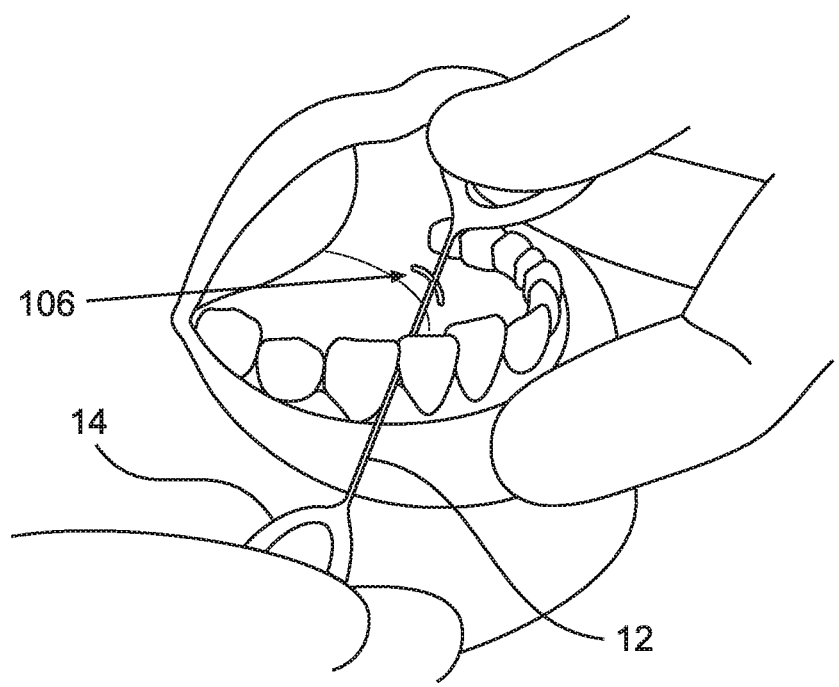

FIG. 5B comprises a perspective pictorial illustration to show how the dental flossing device, being more or less similar to the examples marked in the description as 10, 60, 80, 100, 110, 150, 160, can be inserted into IPSs by the user. Schematically and for example only, one of the handles is marked 14, the flossing strip is marked 12 and the filaments on the strip 12 are marked 106. It is understood, that the flossing device may have various shapes of its handles, flossing strip(s) and filaments, as well as various values of the sections' thickness. FIG. 5B is intended to illustrate that the inventive flossing device is resiliently stretchable, that its flossing strip substantially changes its length and thickness when stretched by the user who grips the handles, so that the stretched flossing strip can be introduced between the lower jaw teeth from above (or between the upper jaw teeth from below).

Upon introducing the flossing strip between the teeth, the flossing is performed by a triple action: 1) moving the device back and forth in the IPS, 2) stretching and contracting/releasing the flossing strip repeatedly, 3) turning the flossing strip around its longitudinal axis. In all the mentioned movements, filaments 106 (or the like) improve the flossing action of the device.

Figure 6A:
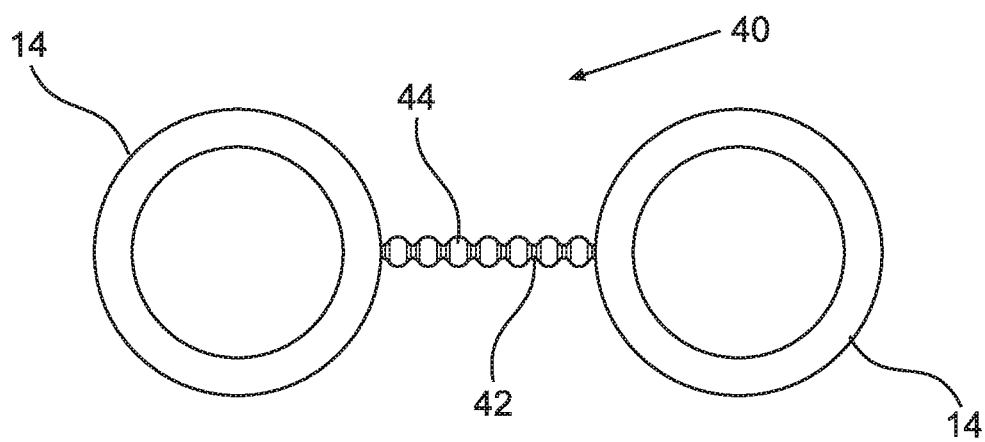
FIG. 6A shows a side view of a sixth embodiment of the invention.

FIG. 6A shows a further embodiment in which a dental flossing device 40 is formed in one piece with the opposing ring-like handles 14 having between them a stretchable elastic central strip 42 with corrugations 44.

Corrugations 44 along the elastic strip 42 assist the user in removing debris from spaces between his teeth. These corrugations 44 are chewable and may dispense either an artificial flavor or a medicine. The corrugations 44 may have various spacing therebetween; they render the strip 42 non-uniform in its thickness. When stretched, the strip 42 may be inserted between the teeth at its narrower section between the corrugations 44, thus alleviating introduction of the strip into any IPS.

It should be mentioned that corrugations, protrusions or filaments, examples of which are shown in the drawings beginning from FIG. 6A, can be provided not only on the flossing strip (and not only on a handle of the illustrated device), but at any member of the inventive device. The device itself may acquire various configurations. Examples of the protrusions, corrugations, filaments, as well as examples of the device configurations can be found in the full set of Figures.

Figure 6B:
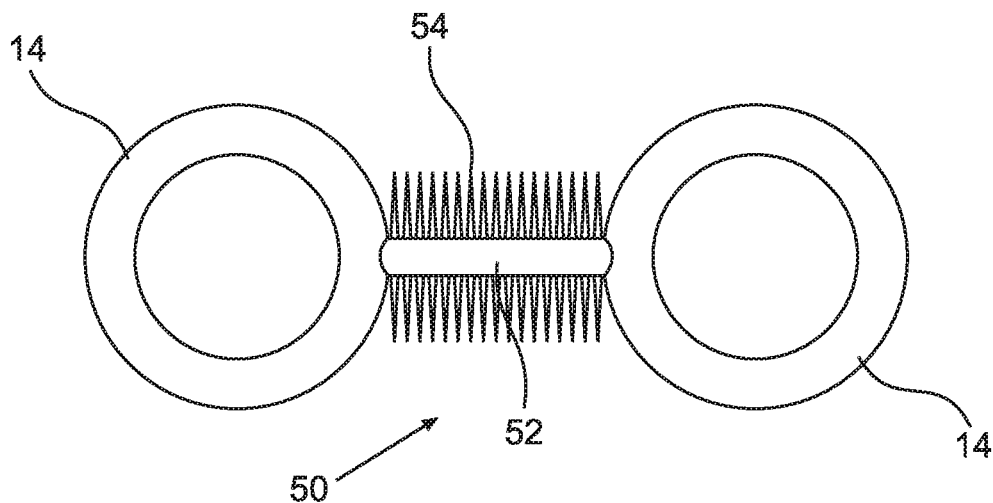
FIG. 6B shows a side view of a seventh embodiment of the invention.

FIG. 6B shows still another configuration in which a one-piece, dental flossing device 50 with the opposing ring-like handles 14 has a central, elastic, strip 52 therebetween. Spirals 54 along the strip 52 assist the user in removing debris from spaces between the user's teeth. Any filaments, for example the spirals 54, may be chewable and dispense either an artificial flavor or a medicine. The spirals constitute one type of filaments.

Figure 7:
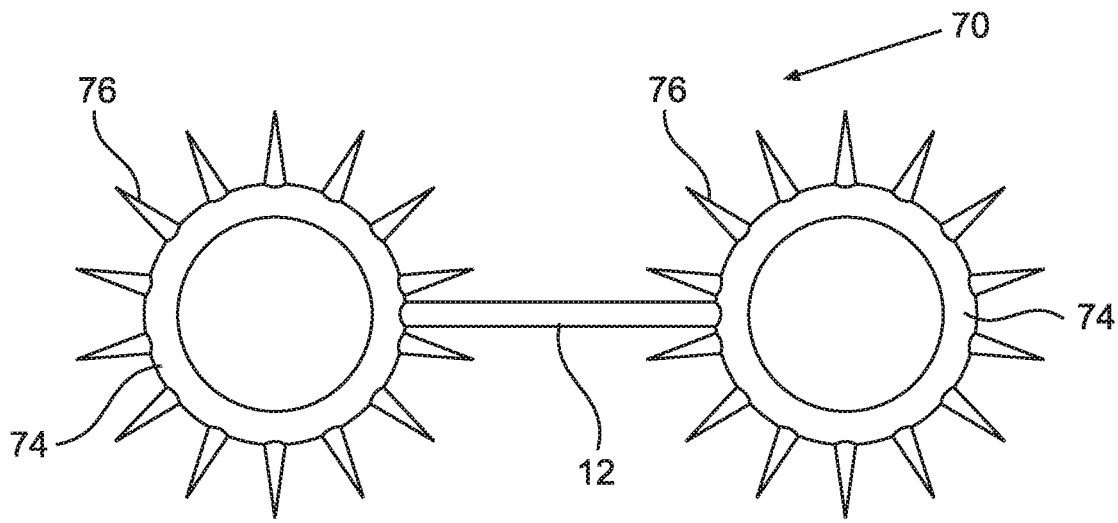
FIG. 7 shows a side view of an eighth embodiment of the invention.

FIG. 7 shows an additional embodiment in which a one-piece dental flossing device 70 with opposing, elastic, ring-like handles 74 has the central strip 12 therebetween. The handles 74 have emanating rays 76 which likewise may be chewable and dispense either an artificial flavor or a medicine.

Figure 8A:
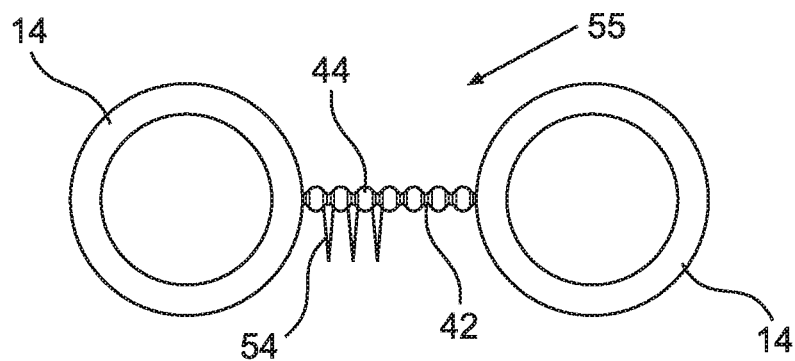
FIG. 8A shows a side view of a ninth embodiment of the invention.

As shown in FIG. 8A by an exemplary configuration 55, spirals 54 and corrugations 44 can be made on the same flossing strip 42.

The resilient elastic flossing strip—for example the strip 12, the strip 42 with its chewable corrugations 44, and the strip 52 with its chewable spirals 54 may also include different drugs or flavors to give the user a medicine or a taste while cleaning the teeth. Flavors like mint, banana, peach, etc. and matching colors of the strip 12, the strip 42, the corrugations 44, the strip 52 and the spirals 54 will give the user different tastes while cleaning the teeth. The proposed stretchable flossing strip (for example the strip 12, the strip 42 with the corrugations 44, the strip 52 and the spirals 54) may further include different drugs which, by their fast release at narrow crevices between the teeth, even for a short period of time, will induce different healing effects. The strip 12, the strip 42, the corrugations 44, the strip 52, the spirals 54, and the rays 76, with either medicines or flavors or both impregnated therein, entice reluctant users, particularly children, to floss whenever needed, thus enhancing their dental hygiene.

Figure 8B:
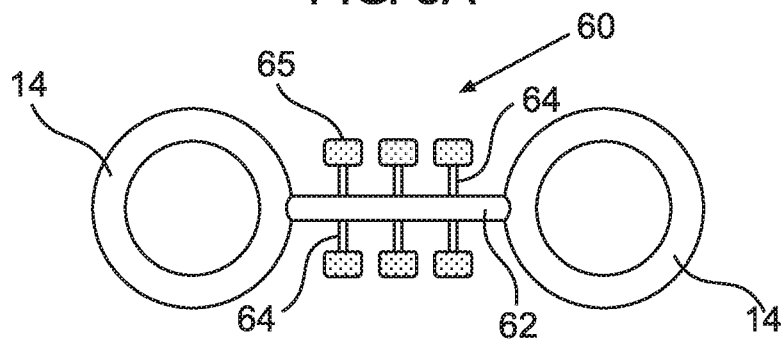
FIG. 8B shows a side/plan view of a tenth embodiment of the invention.

FIG. 8B shows a plan view of yet another embodiment 60 of the invention. The two loop handles 14 are thicker than the resiliently stretchable flossing strip 62 which is provided with three pairs of filaments 64 located at its middle portion and radially extending from the strip. All the filaments 64 lay in one plane being common with the plain of the loop handles. Optionally, the filaments 62 may have endings (shown by dotted lines). In this figure, the filaments are shown as having rectangular roughened endings (plates) 65 to increase their friction with food residuals, when the flossing strip is inserted in IPS. In this drawing, all the filaments 64 are shown as laying in one plane, though at least some of them may be designed to lay in another plane, non-coinciding with that of the others, for example one or both of the middle filaments may be perpendicular to other ones.

The plates 65, as well as other filaments' endings which will be shown in further figures, serve not only for better cleaning, but also for gums massage when using the flossing device. Moreover, any filaments may comprise impregnated medicine or other active material for healing, disinfecting, and/or deodorating the patient's teeth and gums during the flossing.

Figure 8C:
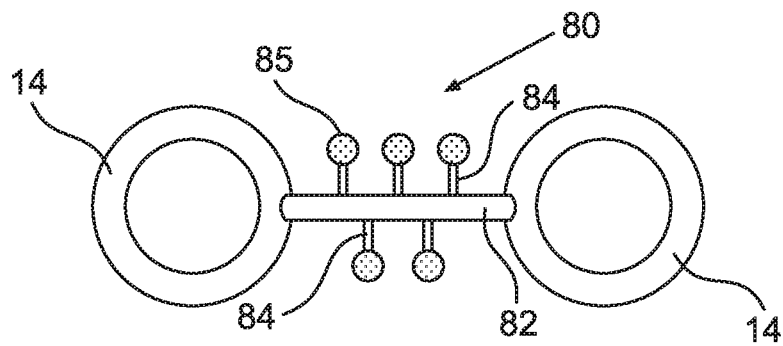
FIG. 8C shows a plan view of a eleventh embodiment of the invention.

FIG. 8C shows a plan view of a next embodiment 80 of the invention. Filaments 84 radially extend from the flossing strip 82, form two groups longitudinally shifted in respect of one another and have roughened ball-like endings 85 to increase their friction with food residuals in IPS. As above, the filaments are shown as laying in one plane, though they may lay in non-coinciding planes.

Figure 8D:
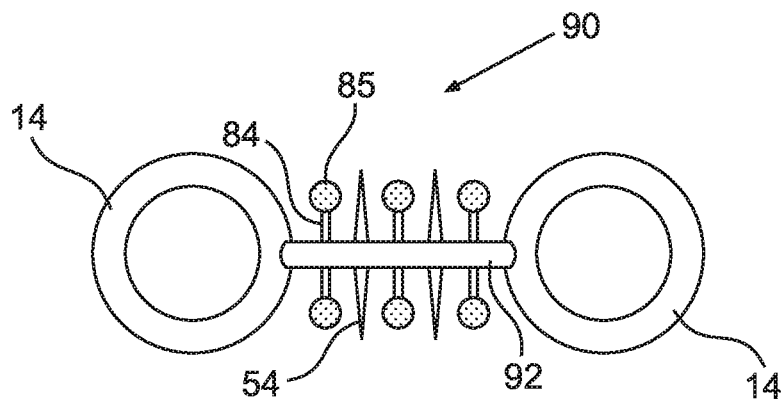
FIG. 8D shows a plan view of a twelfth embodiment of the invention.

FIG. 8D shows a plan view of a further implementation 90 of the invention. In contrast with the above-illustrated examples, filaments of that embodiment are clearly divided into two types. Filaments or spirals 54 of a first type have sharpened endings, while filaments 84 of the second type have ball-like endings 85. Different filaments are interleaved. As above, the radially extending filaments may lay either in one plane or in different planes. The sharp filaments are more active in cleaning the debris, while the ball-ended filaments are more effective in massaging the gums.

Figure 9:
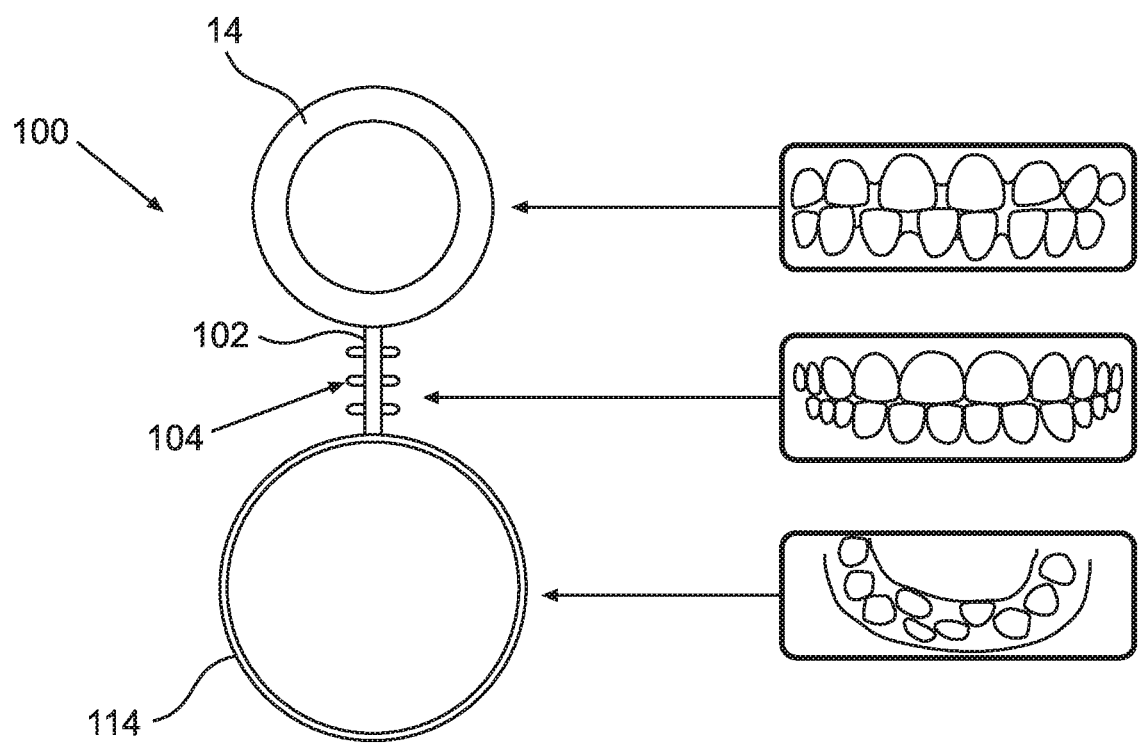
FIG. 9 shows a schematic view of an additional embodiment of the invention, being an example of a so-called three-in-one flossing device.

Beginning from FIG. 9, the figures illustrate the inventive flossing devices, in which their elements/members intentionally have different values of thickness. Due to that, different elements of the flossing device may be used for cleaning different IPSs. For example, quite universal flossing modules "three-in-one" comprising two handles and a bridging flossing strip (or 2 strips) of different thicknesses are shown in FIGS. 9, 10, 14A, 14B, 15, 16.

Proposed and recommended dimensions of the proposed devices and their elements will be presented at the end of the detailed description.

FIG. 9 shows a schematic plan view of an additional implementation 100 of the invention, where two loop-like handles have different thicknesses and are connected by a single stretchable flossing strip 102 having thickness differing from that of any of the handles 14, 114. The handles and the flossing strip can serve as three flossing members which respectively suit to IPSs having different dimensions. According to this Figure, the thick handle 14 can be used for spaced teeth, the medium flossing strip 102 can be used for regular teeth, and the thin handle 114 can be used for crowded teeth (which is illustrated by suitable pictorial fragments near corresponding sections of the configuration 100. Filaments 104, shown on the flossing strip 102, are optional and may have various shapes.

Figure 10:
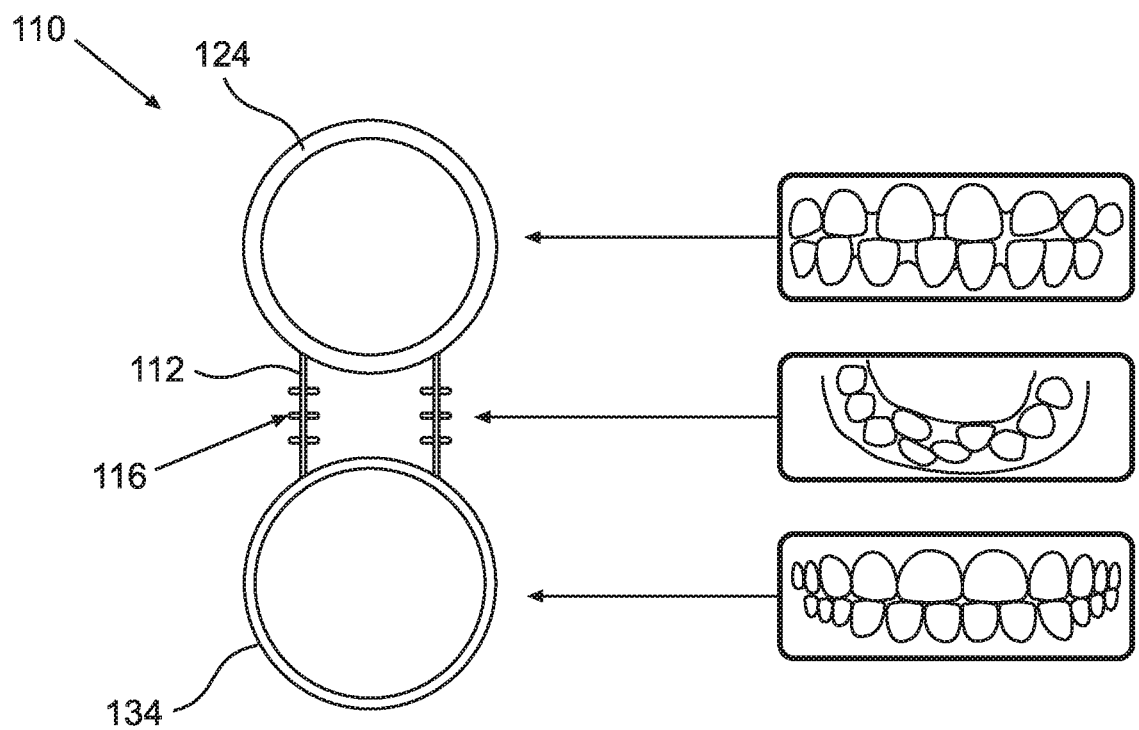
FIG. 10 shows a schematic view of yet another additional embodiment of the invention, comprising two parallel flossing strips.

FIG. 10 shows a schematic front view of yet additional configuration 110 of the invention, where the two loop-like handles 124, 134 are connected by a pair of stretchable elastic flossing strips 112. In this specific embodiment, the two handles have different thicknesses, the two flossing strips 112 are thinner than any of the handles, thinner than a regular medium strip, and are placed in parallel to one another. Such extra-thin flossing strips can be used for very crowded teeth. The Inventors have arrived to the illustrated configuration 110 upon recognizing the fact that when the extra-thin strips are needed, they should be arranged at least in pairs between the handles, otherwise they will be torn quickly. The filaments 116 are shown as an example, and are of course optional.

Figure 11:
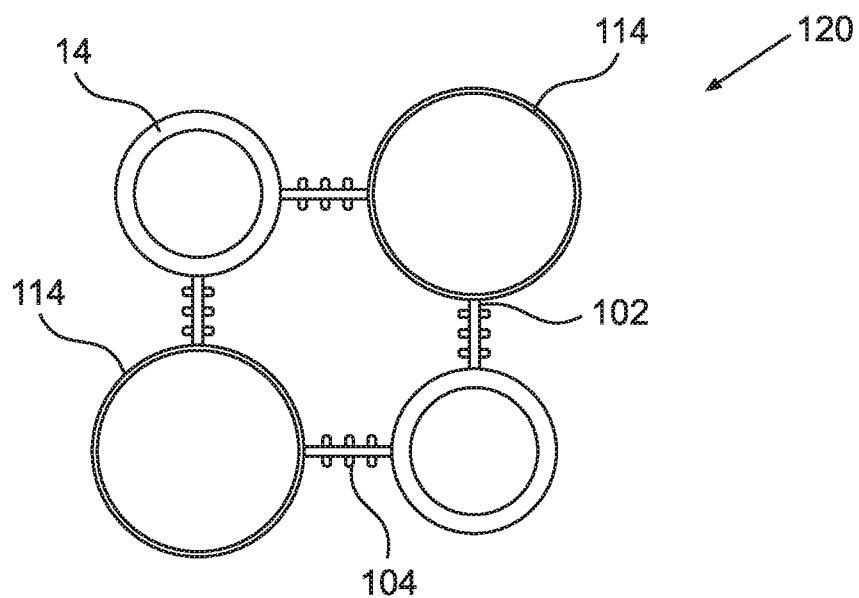
FIG. 11 shows a plan view of an exemplary ring-like configuration of the flossing device.

FIG. 11 shows a front view of an exemplary matrix-like (or ring-like) configuration 120 of the stretchable elastic flossing device, where three or more loop-like handles (say, four handles of the types 14, 114) are connected in a ring by more than two flossing strips 102. As can be seen, the loop-like handles have different thickness values. Alternatively or in addition, the handles may have different profiles, e.g. at least some of them may be flattened rings. Such a flattened ring (see for example 144 in FIG. 14B) has a crossection with different values of thickness along two mutually perpendicular axes, and thus may be inserted into different IPSs.

Figure 12:
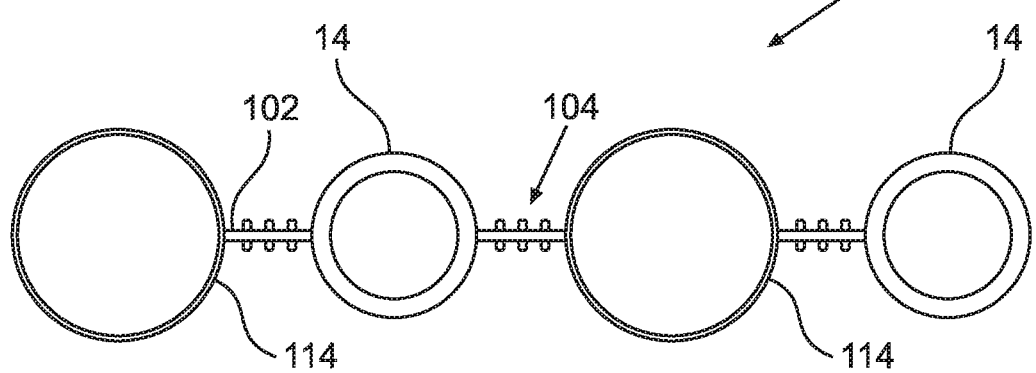
FIG. 12 shows a plan view of an exemplary chain-like configuration of the flossing device.

FIG. 12 shows a view of another exemplary implementation 130 of the stretchable elastic flossing device, where more than two loop-like handles (for example, two handles 14 and two handles 114) are connected by more than one flossing members (say, 102) into a chain. The handles and the flossing strips may have different thickness values and may also have different profiles and different filaments. The chain 130 may be manufactured as quite a long integral structure. Suitable flossing modules may be then cut from chain 130 by a user, as desired. The matrix 120 can be made and used similarly.

Figure 13:
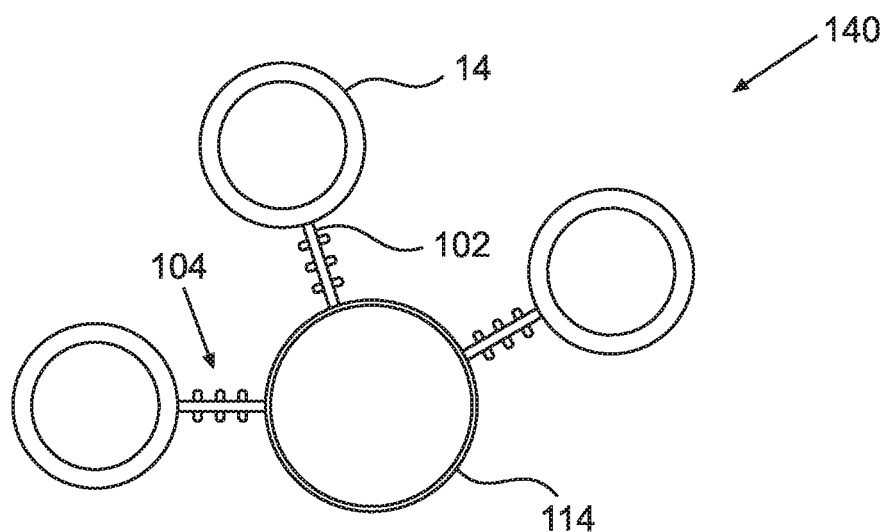
FIG. 13 shows a plan view of an exemplary star-like configuration of the flossing device.

FIG. 13 shows a plan view of an exemplary star-like configuration 140 of the stretchable elastic flossing device, where three or more loop-like handles e.g. 14, 114, 124, 134, etc. are interconnected by two or more flossing strips radially extending from one of the handles, say 114. Different members of the device may have different thicknesses, profiles, filaments. "Rays" of the star 140 may be chains like 130.

Figure 14A:
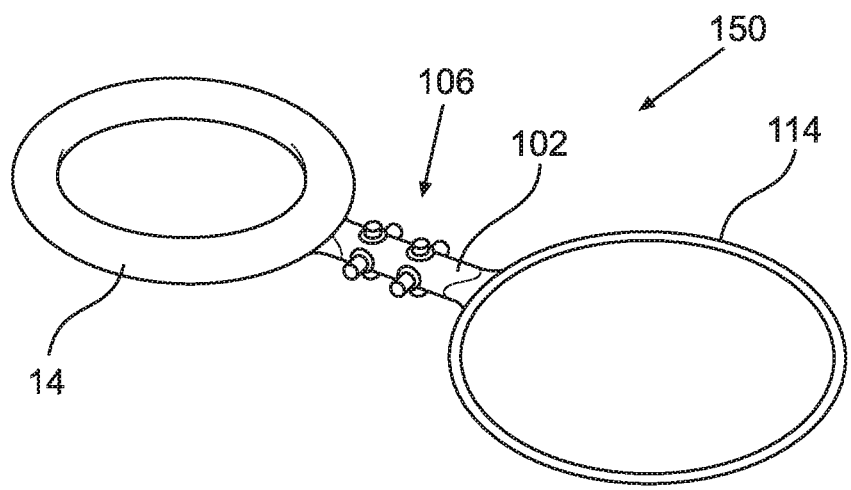
FIG. 14A shows a perspective view of one specific embodiment of the invention, similar but not identical to that in FIG. 9.

FIG. 14A shows a perspective view of one specific embodiment 150 of the invention, similar but not identical to that in FIG. 9. The device is a gummy floss "3-in-1", that has three sections/members of different thickness for different areas in the teeth arch. A thick ring-like handle 14 is for spaced teeth, and thin ring-like handle 114 is for crowded teeth and a single stretchable resilient flossing strip 102 of a medium thickness is for regular teeth. The middle section (the strip 102) is provided with protrusions/filaments 106 radially extending from the strip in different planes (3D filaments), and allow a better sweeping mechanism, better cleaning of plaque and food residues, as well as better massaging of gums. The shape of the filaments may be various, some examples of their shape were illustrated in FIGS. 6B-8D. The handle/s may also comprise filaments, see for example the embodiment of FIG. 7.

Figure 14B:
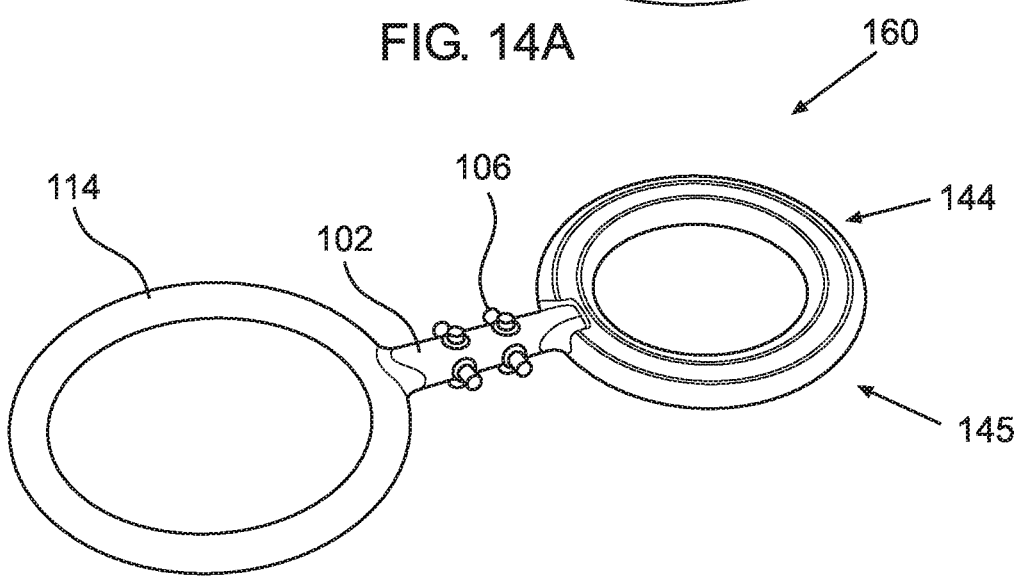
FIG. 14B shows a perspective view of another specific embodiment of the invention, slightly differing from that in FIG. 14A.

FIG. 14B shows a perspective view 14B being a modified implementation of FIG. 14A. In this modification, the handles 14, 144 have different thicknesses and different profiles. For example, one of the handles is a ring 14 having outer diameter of about 14 mm and a circular cross-section (for example, with diameter of about 1.3 mm), while the second handle 144 is a smaller ring (of about 12 mm in diameter with a flattened cross-section which may have width of about 2 mm and height of about 1 mm) The second handle 144 also has profiling ribs 145 on its surfaces, which help to clean suitable IPS. The ribs can be understood as a kind of filaments/protrusions on the handle.

In this embodiment, the flossing strip 102 which bridges the handles is relatively thick (its diameter may be of about 1.50 mm, its length may be of about 6 mm) and has radially extending protrusions 106 similar to those shown in FIG. 14A. Groups of such protrusions lay in mutually perpendicular planes. Spaces between the filaments 106 may be, for example, of about 1.4 mm, while the filaments length may be, for example, of about 1.5 mm.

Figure 15:
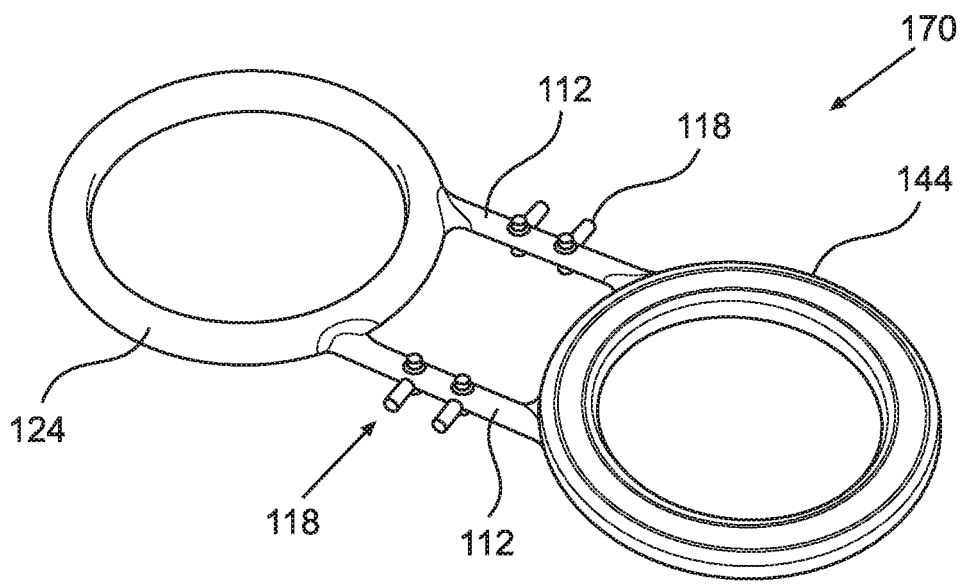
FIG. 15 shows a perspective view of yet another specific embodiment of the flossing device, similar but not identical to that in FIG. 10.

FIG. 15 shows a perspective view of another specific embodiment 170 of the flossing device (similar but not identical to that on FIG. 10), where two relatively thick and large loop-like handles 124, 144 are interconnected by two parallel relatively thin or extra-thin stretchable dental flossing strips 112 with filaments 118. The flossing strips may be spaced from one another by of about 7 mm, while their lengths may be similar (of about 6-7 mm) One of the handles of FIG. 15 is shown as a flattened ring similar to that shown in FIG. 14B, though it may have different (for example, larger) dimensions.

Figure 16A:
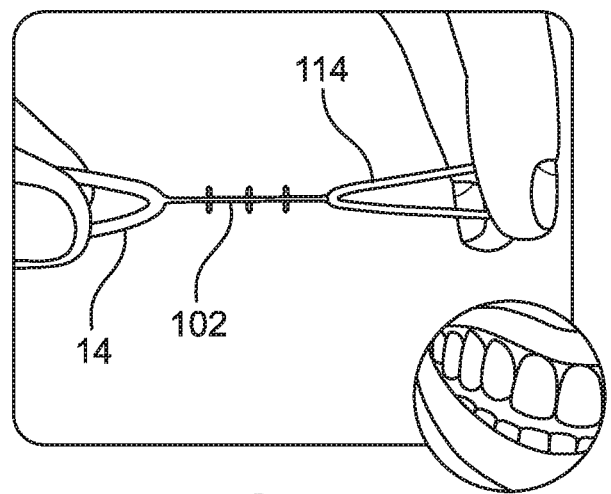
FIGS. 16A, 16B, 16C present pictorial illustrations demonstrating how the inventive three-in-one flossing device can be used.
Figure 16B:
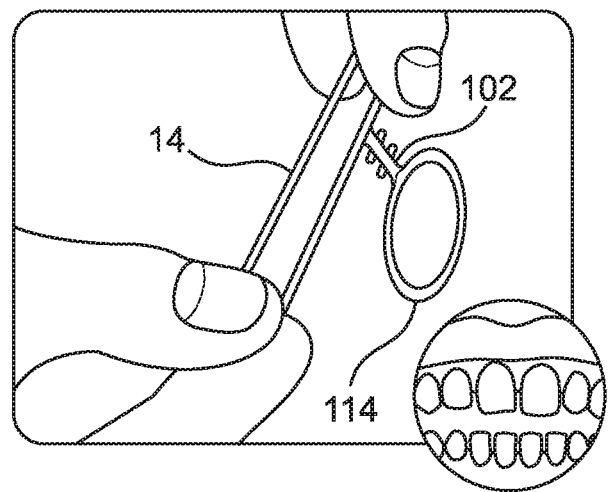
Figure 16C:
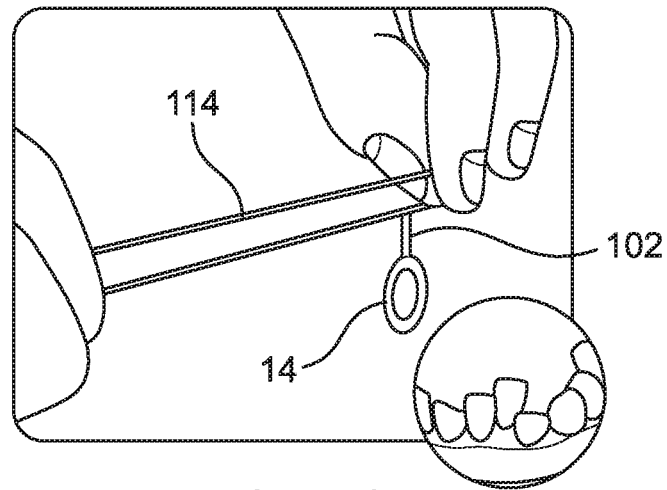

FIGS. 16A, 16B, 16C present pictorial illustrations of the way of using the flossing device, by utilizing an example similar to that shown in FIG. 9.

FIG. 16A shows the stretching action which allows using the middle, stretchable flossing strip of the device (the strip is shown as 102 having a medium thickness) for cleaning IPS between regular teeth.

FIG. 16B shows how a thick loop-like handle 14 of the device can be stretched for use within IPS between spaced (gapped) teeth.

FIG. 16C shows the stretched thin loop-like handle 114 of the device for cleaning IPS between crowded teeth.

The device is used as follows. One of flossing strips or handles of the device is to be gripped and stretched by fingers as needed, and gently inserted (from above or from below) between two adjacent teeth. The thin, middle or thick member (portion) of the device can be used as needed, for each specific IPS space between the teeth. The inserted portion of the device can be moved back and forth, intermittently stretched and contracted to release food residues, thus maximizing the cleaning power of the portion and its filaments (if present). The device may be rinsed and the operation may be repeated to clean all teeth in the both upper and lower jaws.

The flossing device may be used by children, without supervision from age of 7-8. The device may be manufactured in various designs, colors and flavors, as well as with various medical additives. The device is especially useful for children and teenagers, whose teeth are usually a mix of spaced, crowded and regular.

It should be emphasized that relative dimensions of the flossing devices and their elements/members, shown in FIGS. 1-16, are presented as examples only. Dimensions of the proposed inventive devices and their elements (in their original, unstretched state) may vary around the values indicated below:

1. Total length of one flossing module, which comprises two handles bridged by at least one resiliently stretchable flossing strip, may vary between approximate values of (30-50) mm. In some specific examples, the total length may vary between (32-35.5) mm. Various configurations (ring-like, chain like, star-like, etc.) can be designed on the basis of the flossing module.

2. Thickness of loop-like handles may vary in quite a broad range; for convenience this range is presented below for different categories of the handles:
For thin handles, thickness may be approximately (0.4-1.9 mm), in a specific example around 1 mm;
For medium handles, thickness may be approximately (0.75-2 mm), in a specific example around 1.5 mm;
For thick handles, thickness may be approximately (1-3 mm), in a specific example around 2 mm.

3. Diameter of ring-like handles:
For handles with the circular cross-section, outer diameter may be approximately 10-25 mm, for example of about 15 mm.

For handles with a flattened profile, outer diameter may be in the approximate range of 10-15 mm, for example of about 14 mm.

4. Dimensions of the flossing strip/s bridging the two handles:

Length of the flossing strip/s, in the initial unstretched state, varies in an approximate range (3-15) mm, an exemplary length of a specific embodiment is of about 6 mm; Thickness of the flossing strip/s, in the initial unstretched state, varies in an approximate range (0.4-3) mm. In more specific implementations, the thickness of a thin strip may be around 1 mm, of a medium strip—of about 1.5 mm, and of a thick strip—of about 2 mm. Thin strips or extra thin strips may be used in implementations similar to those shown in FIG. 10 or FIG. 15; thickness of extra thin strips can be accordingly selected from the lower sub-range of the proposed range: for example, from an approximate sub-range (0.4-1) mm.

5. Dimensions of filaments:

Length of the filaments varies in an approximate range of 0.75-2.5 mm,

Thickness of the filaments varies in an approximate range of 0.1-0.9 mm,

Space between two adjacent filaments approximately varies between 0.1-1.5 mm.

Plates or balls at the end of filaments may be provided for improving the cleaning function of the flossing device, and for providing massage of the gums in addition to and simultaneously with the cleaning action.

It is noted that the foregoing examples have been provided merely for the purpose of explanation and are in no way to be construed as limiting the present invention. While the present invention has been described with reference to some exemplary embodiments, it is understood that the words which have been used herein are words of description and illustration, rather than words of limitation. Changes may be made, within the scope of the appended claims, as presently stated and as amended, without departing from the scope and spirit of the present invention in all of its various aspects. Although the present invention has been described herein with reference to particular structures, materials and embodiments, the present invention is not intended to be limited to the particulars disclosed herein. Rather, the present invention extends to all functionally equivalent structures, methods and uses, such as are within the scope of the appended claims.

I claim:

1. A dental flossing device comprising elastic handles bridged by at least one elastic flossing strip made of a material resiliently stretchable in a range of 50% to 800% of its original length under a stretching force applied by fingers of a user, while completely returning to its original length when said stretching force is no longer applied, wherein the elastic handles are loops made of a resiliently stretchable material, which handles are adapted to serve as additional flossing members of the device, and wherein the thickness of the material of each of said handles, in the initial state thereof prior to stretching, differs from one another and from the thickness of the material of the stretchable flossing strip, in the initial state thereof prior to stretching, such that each of said handles and said stretchable flossing strip are adapted to be inserted between adjacent lower jaw teeth from above or between adjacent upper jaw teeth from below, the portion of the device selected for insertion between any given pair of adjacent teeth being determined by the dimensions of the inter-proximal space (IPS) therebetween, thereby providing three different portions on the same device, respectively suitable for flossing IPSs of different dimensions.

2. The dental flossing device according to claim 1, including at least one additional resiliently stretchable elastic flossing strip bridging said two elastic handles.

3. The dental flossing device according to claim 1, wherein the material of said flossing strip and of said handles is a silicone rubber resiliently stretchable up to 800% of its original size when subjected to a stretching force.

4. The dental flossing device according to claim 1, wherein the material of said flossing strip and of said handles is an organic rubber selected from the group consisting of latex, SBR, Nitril rubber, and EPDM, or a thermoplastic elastomer selected from the group consisting of SBS, SEBS, and Xantropene.

5. The dental flossing device according to claim 4, wherein the material of said flossing strip and of said handles has a stretchability of from 50% up to 800%.

6. The dental flossing device according to claim 1, further including at least one additional handle and at least one additional flossing strip, the device being arranged in a ring-like configuration, in a matrix-like configuration, in a chain-like configuration or in a star-like configuration.

7. The dental flossing device according to claim 1, wherein the two elastic handles are circular loops, the material of which having different diameters and/or different profiles.

8. The dental flossing device according to claim 1, wherein the material of the flossing strip has a non-uniform thickness, changing along the length of the strip.

9. The dental flossing device according to claim 1, wherein said stretchable flossing strip is provided with protrusions or filaments made of the same material as said strip.

10. The dental flossing device according to claim 9, wherein said protrusions or filaments radially extend from the flossing strip in one or more directions.

11. The dental flossing device according to claim 1, wherein each of said handles is a loop with an elastic web in its center and further wherein the thickness of the elastic web is less than the thickness of the material of each of the loops of the handles.

12. The dental flossing device according to claim 1, being chewable and dispensing an artificial flavor or a medicine.

13. A method of manufacturing a dental flossing device, comprising:

molding at least one elastic flossing strip insertable into inter-proximal spaces (IPSs) of the user's teeth and resiliently stretchable by a user in a range of 50% to 800% of its original length, said strip having a right terminal end and a left terminal end;

integrally molding an elastic right handle with the right terminal end of the strip; and integrally molding an elastic left handle with the left terminal end of the strip;

wherein the strip and the handles are formed into a single piece out of the same suitable elastic material;

wherein the elastic handles are resiliently stretchable loops adapted to serve as additional flossing members of the device;

and wherein the thickness of the material of each of said handles, in the initial state thereof prior to stretching, differs from one another and from the thickness of the stretchable flossing strip, in the initial state thereof prior to stretching, such that each of said handles and said stretchable flossing strip are adapted to be inserted between adjacent lower jaw teeth from above or between adjacent upper jaw teeth from below, the portion of the device selected for insertion between any given pair of adjacent teeth being determined by the dimensions of the IPS therebetween, thereby providing three different portions on the same device, respectively suitable for flossing IPSs of different dimensions.

14. The method according to claim 13, further including molding at least one additional elastic flossing strip and at least one additional elastic handle out of the same suitable elastic material and integrally molding all said elastic flossing strips and all said elastic handles into a single piece so as to form a ring-like, a matrix-like, a chain-like or a star-like structure.

15. The device according to claim 1, wherein the handles are provided with protrusions or filaments made of the same material of the handles.

16. The device according to claim 1, being a 3-in-1 device having three flossing members of different thickness for flossing between regular, crowded and/or spaced teeth, as required.

\* \* \* \* \*